April 5, 1960 W. A. WOOD Plant Pat. 1,930
APPLE TREE
Filed Dec. 31, 1958
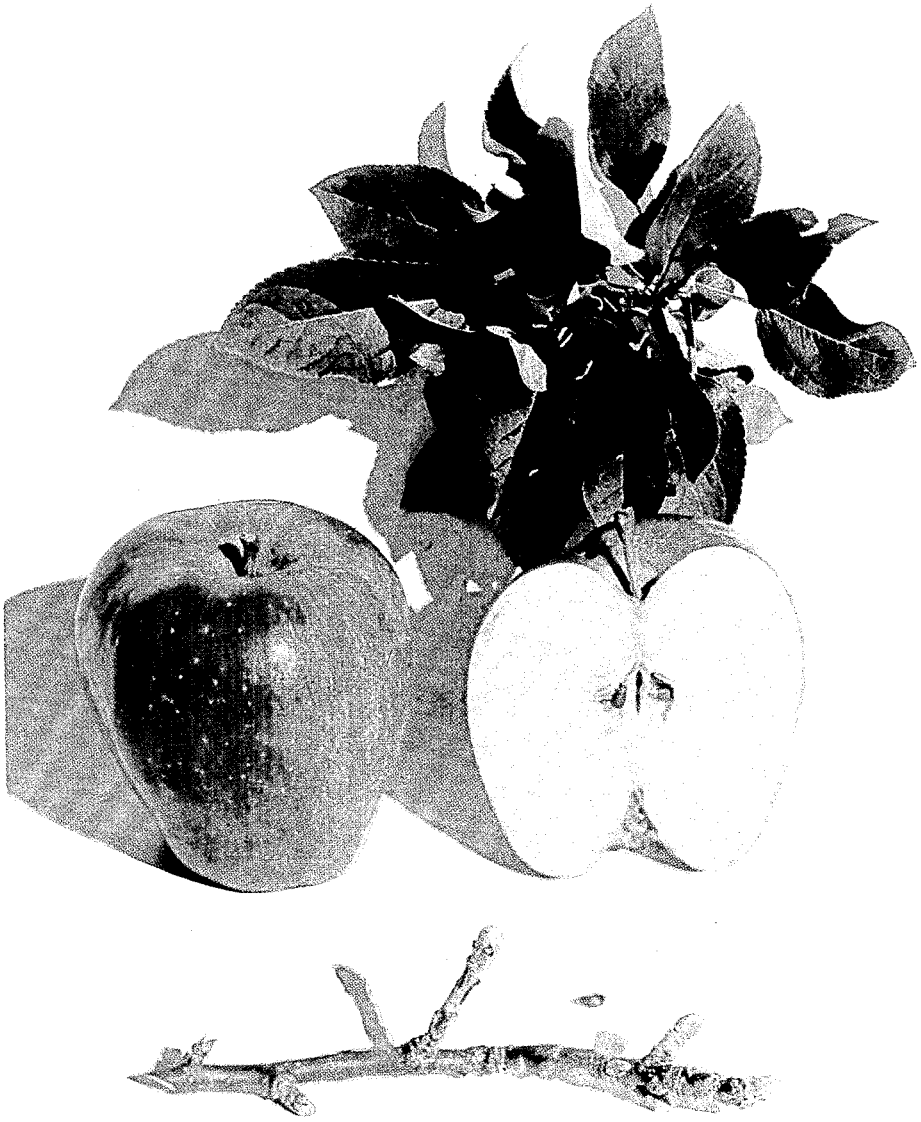
INVENTOR
Walter A. Wood
BY Cobb & Cobb
ATTORNEYS United States Patent Office Plant Pat. 1,930
Patented Apr. 5, 1960

1,930

APPLE TREE

Walter A. Wood, Winthrop, Wash., assignor to Stark Bro's Nurseries and Orchards Company, Louisiana, Mo., a corporation of Missouri Application December 31, 1958, Serial No. 784,411

1 Claim. (Cl. 47—62)

The present invention relates to a new and distinct variety of apple tree which was discovered by me as a bud sport of the variety which has long been sold in commerce under the trademark "Starking Delicious" (unpatented), said discovery having been made in my cultivated orchard which is located near Winthrop, Washington.

At the time of my discovery, I was growing in my orchard aforesaid a block of apple trees of the variety known as "Starking Delicious," and while engaged in routine care of the orchard, my attention was attracted to one tree which appeared to be clothed with unusually dark green foliage, and which was more stocky in its habit of growth and bore more fruit spurs than the other adjoining trees of "Starking Delicious." Closer observation of the particular tree aforementioned convinced me that it was a whole tree mutation of "Starking Delicious" and I thereupon promptly took steps to preserve the same and to keep it under close observation.

Continued observation showed that this new sport bore fruit which colored at least a week or more earlier than the fruit of adjoining "Starking Delicious" trees, as determined by my inspection of the orchard for the purpose of scheduling the time for picking the crop of applies growing in the orchard.

Further observations and tests of the new sport over a period of several years have conclusively demonstrated that the sport is definitely a new and distinct variety and is particularly characterized as to novelty by the following unique combination of features which are outstanding in the new variety and which distinguish it from "Starking Delicious," as well as from all other varieties of which I am aware:

(1) Smaller tree size and more upright habit of growth than "Starking Delicious," but with a habit of developing more fruit spurs and consequently resulting in greater fruit production;

(2) Development of fruit spurs at an earlier age than "Starking Delicious," with consequent earlier production of fruit; and (3) Fuller and earlier development of red color of the fruit by at least 1 week or more earlier than "Starking Delicious," with the color being a deeper red and occurring in an over-all striped pattern as distinguished from the less intense and less completely striped coloring of the fruit of "Starking Delicious."

Asexual reproduction of the new variety by budding, as performed by me in my orchard near Winthrop, Washington, shows that the foregoing characteristics and distinctions come true to form and are established and transmitted through succeeding propagations.

The accompanying drawing shows typical specimens of the foliage and fruit of my new variety, as well as the fruiting spur growth of a typical branch section, and with one of the fruit specimens shown in cross-section, all as depicted in color as nearly true as it is reasonably possible to make the same in a color illustration of this character.

The following is a detailed description of my new variety, with color terminology in accordance with Ridgway's Color Standards and Nomenclature (hereinafter abbreviated as "Ridgway") and the Horticultural Color Chart (hereinafter abbreviated as "HCC"), except where general color terms of ordinary dictionary significance are obvious:

(Observations made from specimens grown near Winthrop, Okanogan County, Washington.)

Dates of first and last pickings: From about September 30th to about October 5th.

Tree: Medium small; medium vigorous; upright; medium low; vase-formed; slow-growing; hardy; very productive; regular bearer.

*Trunk.*—Smooth; stocky.

*Branches.*—Smooth; thick; little-branching. Color—Dark Livid Brown, Plate XXXIX, Color No. 1‴, tone *k* (Ridgway). Lenticels—medium; medium large.

*Leaves.*—Medium large; medium width; medium length; ovate; abruptly pointed; thick; rugose. Average length—3½ inches. Average width—2 inches. Color—Parsley Green, Plate 00962, page 193, vol. 2 (HCC). Margin—coarsely serrate. Petiole—medium long (about 1 inch); medium thickness.

Flowers:

*Dates of first and full bloom.*—May 6th and May 10th respectively; medium early as compared with other varieties.

*Size.*—Medium large.

*Color.*—White, with portions of petals tinged with Carmine, Plate 21/3, page 21, vol. 1 (HCC).

Fruit:

*Maturity when described.*—Hard-ripe; date October 22nd.

*Size.* — Uniform. Axial diameter — 3⅛ inches. Transverse diameter—3 inches.

*Form.*—Conical; truncate at base; slightly angular.

*Cavity.*—Symmetrical; obtuse; even; pubescent toward apex. Depth — ½ inch. Breadth — 1¼ inches. Markings: color—Light Yellowish Olive, Plate XXX, Color No. 23″, tone *i* (Ridgway).

*Basin.*—Symmetrical; flaring base; wide; furrowed; pubescent. Depth—½ inch. Breadth—¼ inch. Markings—stripes of Light Yellowish Olive, Plate XXX, Color No. 23″, tone *i* (Ridgway).

*Stem.* — Clubbed; medium stout; pubescent. Length—1 inch. Breadth—⅛ inch.

*Calyx.*—Closed; segments persistent; broadly lanceolate; acute; 5/16 inch long; segments approximate; converged from base toward center; both outer and inner surfaces pubescent.

*Skin.*—Thick; tough; smooth; waxed. Dots: obscure; many; small; depressed; circular; color—Cartridge Buff, Plate XXX, Color No. 19″, tone *f* (Ridgway); distribution—distributed over entire surface, but most numerous below middle. Ground color—Chartreuse Green, Plate 663, page 90, vol. 1 (HCC). Color of markings—Claret Rose, Plate 021, page 109, vol. 2 (HCC), with stripes of Indian Lake, Plate 826, page 170, vol. 2 (HCC).

*Bloom.*—Wanting.

*Scarfskin.*—Wanting.

*General color effect.*—Bright over-all striped red.

*Flesh.*—Rather juicy. Color—satiny white, with greenish tinge. Texture—firm; fine; crisp. Flavor—mild; rich. Aroma—distinct. Quality—best.

*Core.*—Median. Bundle area—medium large; cordate; symmetrical at base; acute at base. Halves of core—equal. Bundles—in one whorl; color—Sap Green, Plate 62, page 62, vol. 1 (HCC). Core lines—clasping; indistinct in cross section. Carpellary area—distinct; small. Calyx tube: pubescent toward base; funnel form; stem of funnel long; depth of tube to shoulder—¼ inch; entire depth—9/16 inch. Styles—present. Stamens—in one distinct whorl; median. Seed cells: axile, open; cell walls—thick, tough; length—⅞ inch, breadth—½ inch; longitudinal section—orbicular; cross section—broad; surface—fissured.

Seeds:

*Average number.*—From 6 to 8 perfect; none imperfect; 2 per cell. Length—5/16 inch. Breadth—3/16 inch.

*Form.*—Acute.

*Color.*—Chestnut Brown, Plate XIV, Color No. 11", tone *m* (Ridgway).

Use: Market; dessert.

Keeping quality: Good; about 110 days in ordinary storage.

I claim:

A new and distinct variety of apple tree, substantially as herein shown and described, characterized particularly as to novelty by the unique combination of a smaller tree size and more upright habit of growth than the variety "Starking Delicious" (unpatented), but having a habit of developing more fruit spurs with consequent greater fruit production, an earlier development of fruit spurs than the variety "Starking Delicious," with a consequent fruiting habit at an earlier age, and a fuller and earlier development of red color of the fruit, said color being a deeper red and appearing in a more over-all striped pattern than in the fruit of "Starking Delicious."

References Cited in the file of this patent

UNITED STATES PATENTS

P.P. 1565 Bisbee ---------- Feb. 12, 1957